(12) United States Patent
Nieuwenhuizen et al.

(10) Patent No.: US 6,638,542 B2
(45) Date of Patent: Oct. 28, 2003

(54) REDUCING APPETITE IN MAMMALS BY ADMINISTERING PROCYANIDIN AND HYDROXYCITRIC ACID

(75) Inventors: Arie Gijsbert Nieuwenhuizen, Utrecht (NL); Katrien Maria Jozefa Van Laere, Heteren (NL)

(73) Assignee: Nutricia N.V., Zoetermeer (NL)

( * ) Notice: Subject to any disclaimer, the term of this patent is extended or adjusted under 35 U.S.C. 154(b) by 0 days.

(21) Appl. No.: 09/956,463

(22) Filed: Sep. 20, 2001

(65) Prior Publication Data

US 2003/0064937 A1 Apr. 3, 2003

(51) Int. Cl.[7] .................. A01N 65/00; A61K 35/78
(52) U.S. Cl. ................ 424/732; 424/735; 424/736; 424/776
(58) Field of Search ................ 424/735, 732, 424/736, 770, 769, 771, 776, 775, 70.11; 435/390, 410, 411, 412, 267; 426/21, 49, 51, 288, 270, 615, 616, 617, 419, 481

(56) References Cited

U.S. PATENT DOCUMENTS

| | | | | |
|---|---|---|---|---|
| 3,989,822 A | * | 11/1976 | Whistler | 424/180 |
| 5,911,992 A | * | 6/1999 | Braswell et al. | 424/195.1 |
| 6,294,190 B1 | * | 9/2001 | Nakahara et al. | 424/442 |
| 6,297,273 B1 | * | 10/2001 | Romanczyk, Jr. | 514/456 |

FOREIGN PATENT DOCUMENTS

| | | | |
|---|---|---|---|
| WO | WO 00/54610 | * | 10/2000 |

* cited by examiner

Primary Examiner—David M. Naff
Assistant Examiner—Deborah K. Ware
(74) Attorney, Agent, or Firm—Young & Thompson

(57) ABSTRACT

Procyanidin, optionally combined with hydroxycitric acid, is used in a method for the reduction of appetite in a mammal. Preferably procyanidin is administered to the mammal in a dosage of between 0.5 and 100 mg per kg bodyweight. Also shown is a process for the manufacture of an appetite reducing composition.

10 Claims, 2 Drawing Sheets

Figure 1: Relative food intake after administration of 3.5, 6.5, 13 and 26 mg procyanidin per kg rat when compared with the placebo treatment.
☐ 3.5 mg procyanidin per kg rat
▨ 6.5 mg procyanidin per kg rat
▩ 13 mg procyanidin per kg rat
■ 26 mg procyanidin per kg rat
★ significant difference (p<0.05)
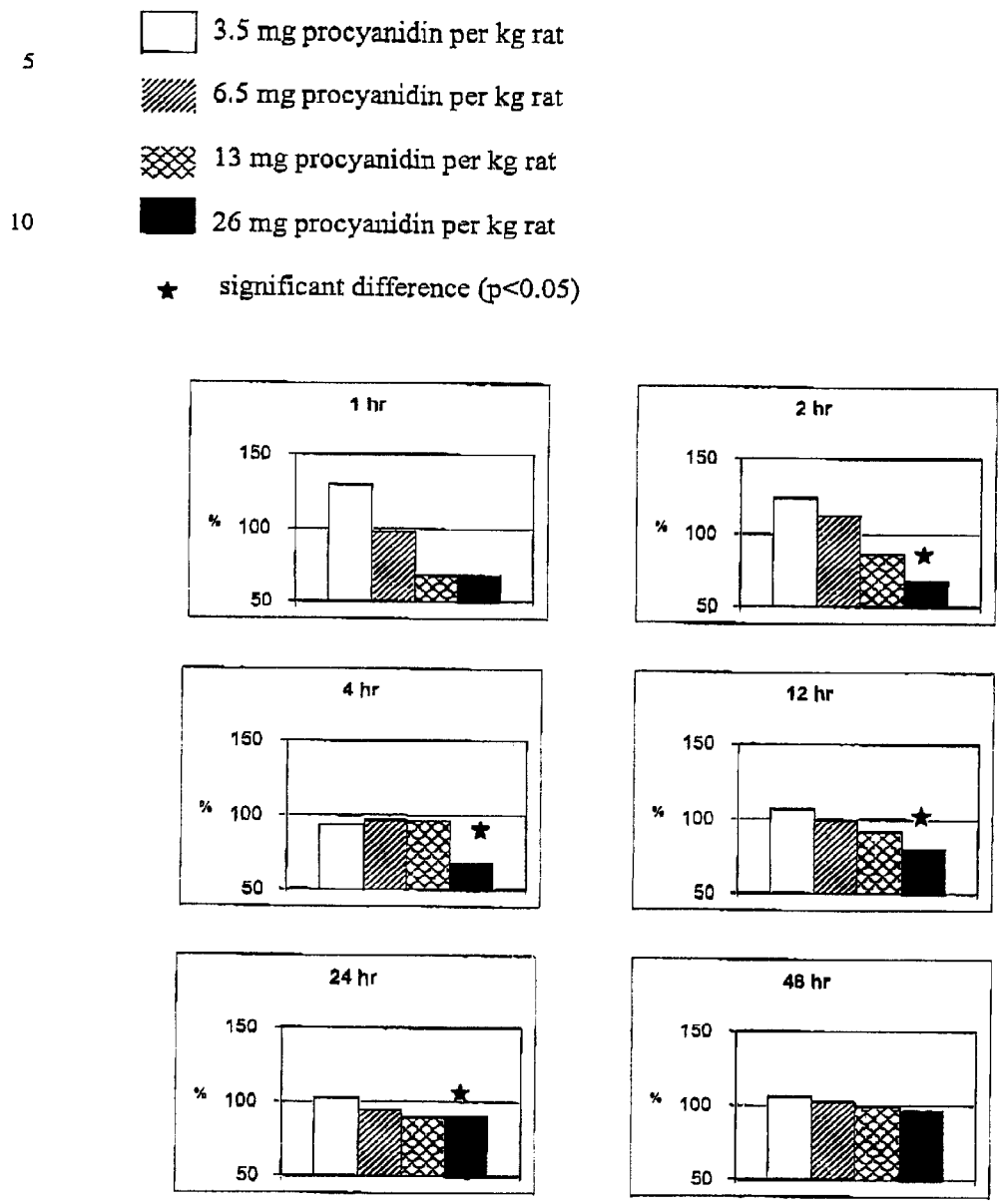

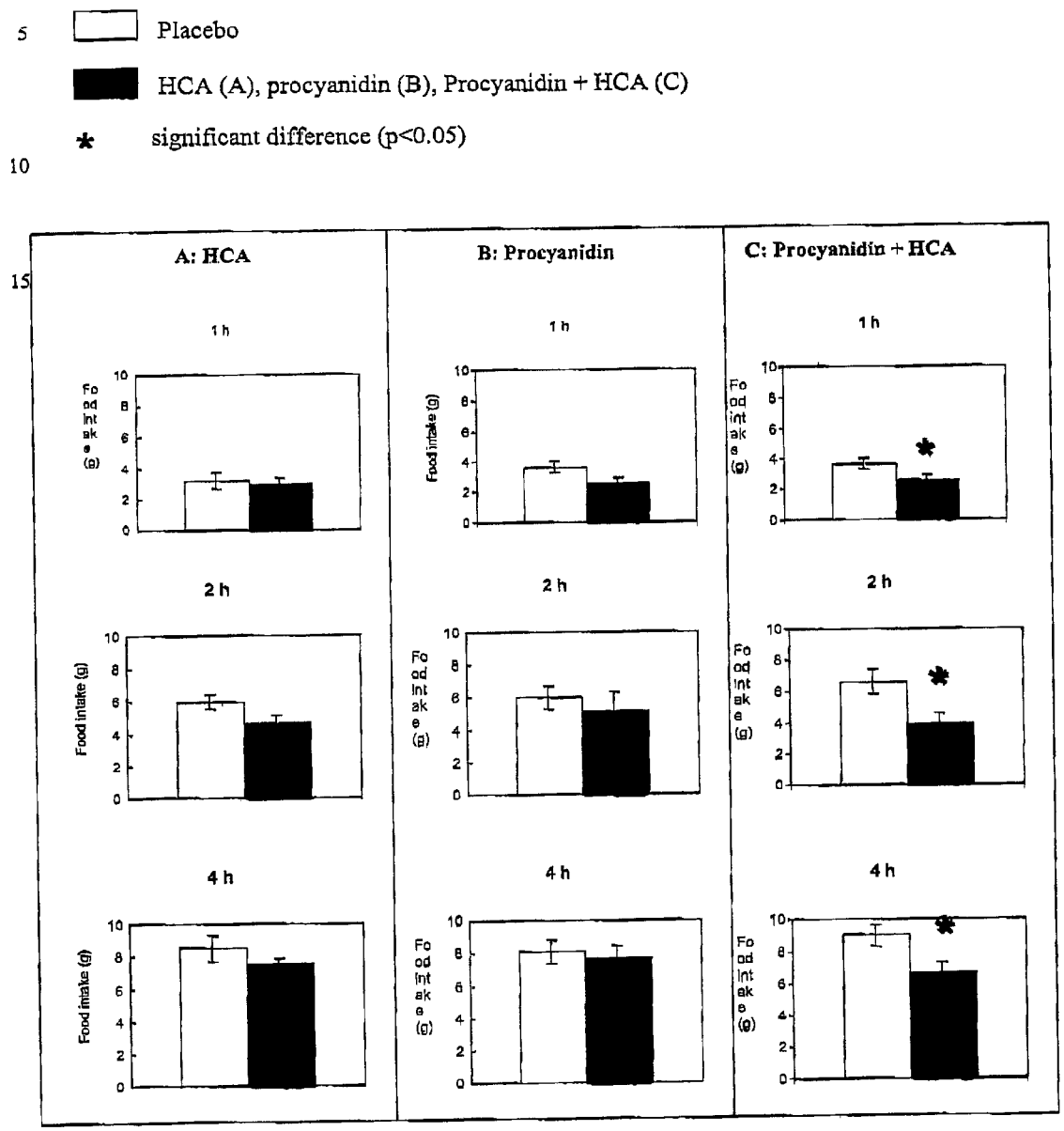
Figure 2: Absolute cumulative food intake compared to placebo after 1,2 and 4 hour administration of hydroxycitric acid (A), procyanidin (B) and procyanidin and hydroxycitric acid (C).
☐ Placebo
■ HCA (A), procyanidin (B), Procyanidin + HCA (C)
* significant difference ($p<0.05$)

REDUCING APPETITE IN MAMMALS BY ADMINISTERING PROCYANIDIN AND HYDROXYCITRIC ACID

FIELD OF THE INVENTION

The present invention relates to a method for reducing the appetite in mammals. More specifically, the present invention relates a method for the reduction of appetite in mammals, said method comprising administering procyanidin to the mammal, optionally combined with hydroxycitric acid, in an appetite reducing amount.

DESCRIPTION OF THE PRIOR ART

Overweight and obesity are major problems within the Western community. Due to increased consumption, decreased exercise and changes in the nutritional value of foodstuffs, many humans and companion animals are suffering from overweight or have difficulty maintaining a desirable weight. Many methods have been proposed to solve these problems, for example via the administration of functional ingredients (e.g. nutritional supplements) which facilitate the reduction of overweight.

Ingestion of functional ingredients can contribute to the loss of weight or the maintenance of a desirable weight in a variety of ways. A popular way of loosing weight is the ingestion of thermogenic components, such as ephedrine. Alternatively, weight modification can be induced by influencing the digestive enzyme activity in an attempt to decrease the absorption of caloric nutritional components from ingested foodstuff. Well-known examples of such actions include the inhibition of intestinal carbohydrases or lipases. Other functional ingredients influence the absorption of nutritional molecules without decreasing intestinal enzyme activity. A further effective method for reducing overweight and obesity can be accomplished by the reduction of food intake, for example, by reducing the desire for food through the ingestion of appetite reducing functional ingredients.

EP815857 describes an antiobestic agent comprising as the active ingredient tamarind seed coat extracts (procyanidin). According to this application, the tamarind seed coat extract or procyanidin can act as a carbohydrase inhibitor, blood sugar increase inhibitor, monosaccharide absorption inhibitor, cholic acid adsorptive excretion promoter, cholesterol lowering agent, blood triglyceride lowering agent and lipase inhibitor.

WO0054610 describes a food complement for dietetic and/or cosmetic purposes, containing anti-lipase properties, for oral administration. Said food complement is characterized in that it comprises a grape extract rich in or enriched with polyphenols.

Several products are currently on the market advertised to induce weight reduction, some including hydroxycitric acid for reduction of the appetite and minor quantities of procyanidin containing extracts having antioxidant activity. Sunshine Slender™ and T. J. Clark's Advanced Liquid Weight Loss Formula™ are examples of such products.

As mentioned herein before, weight reduction can be induced via ingestion of a variety functional ingredients. Severe downsides are attached to the application of functional ingredients which affect digestive pathways. Several functional ingredients modify the uptake of nutrients in vivo in an attempt to reduce caloric uptake. The main disadvantage of such procedure is the alteration of the intestinal uptake mechanisms, which may result in a decreased uptake of essential nutrients. Other functional ingredients act on metabolic pathways that induce the breakdown of excess body fat. In general, such components do not exclusively act as body fat reducers, but also can have severe side effects on other organs (e.g. heart). When reducing the food intake through the ingestion of appetite reducing agents, the disadvantageous side effects associated with the aforementioned functional ingredients, are not experienced.

However, known appetite reducing agents also have undesirable side effects. Fenfluramine and sibutramine act on neurotransmitters in the brain, thereby inducing several adverse side effects. Combinations such as ephidrine and caffeine are also known to have appetite reducing effects, however have also been suggested to have adverse side effects. Therefore there remains a vast interest for safe, affordable and effective appetite suppressing functional ingredients with limited side effects.

SUMMARY

The present invention discloses a method for reducing appetite in mammals comprising administering to said mammals, appetite reducing dosages of functional ingredients which are safe, are deemed not to have disadvantageous side effects, are affordable and plant derived.

The present invention relates to a method for the reduction of appetite in mammals through administering to said mammals and effective dose of procyanidin. Procyanidins, which have, until now, been used mainly for their antioxidant and carbohydrase inhibitory activity, were surprisingly found to have appetite-reducing properties. The present invention provides in a novel therapeutic and/or cosmetic use of procyanidins, optionally combined with hydroxycitric acid (HCA). Optimal usage of the appetite reducing properties of procyanidin can be achieved through administering procyanidin, optionally combined with HCA, in an amount effective to reduce the appetite, not during the consumption of a meal, but some time after the meal, e.g. when experiencing first feelings of appetite or hunger.

The present invention provides in the demand for an effective appetite reducing agent which is safe.

Without wishing to be bound by any theory, it is the inventors belief that the three main pathways by which glucose is metabolized are: A) oxidation in order to yield energy; b) conversion into fatty acids (de novo lipogenesis), a process which mainly occurs in the liver and c) conversion into glycogen, a process which mainly occurs in the liver and skeletal muscle.

It was suggested by the current inventors that procyanidins inhibit the uptake and oxidation of glucose by peripheral tissue, thereby increasing the availability of glucose for the conversion of glucose into glycogen in the liver. The increased glycogen formation is thought to have an appetite reducing effect. Hydroxycitric acid is thought to decrease the formation of fatty acids from glucose (de novo lipogenesis) thereby stimulating the storage of glycogen in the liver and inducing an appetite reducing effect. The complementary action of procyanidins and hydroxycitric acid on different metabolic pathways (glucose oxidation and fatty acid formation respectively) could explain the synergistic action that has been observed by the present inventors. The inhibition of either one of the above "glucose consuming" pathways would not lead to such a significant increase in the glycogen storage in the liver, since the effect of the inhibition of one pathway could be compensated for through the increase of the other glucose consuming pathway. Inhibition of both pathways, however, may well be responsible for the unexpected appetite inhibiting effect resulting from the combined administration of procyanidin and hydroxycitric acid.

BRIEF DESCRIPTION OF THE DRAWINGS

FIG. 1 relates to a series of graphs that show relative food intake of a subject after administration of 3.5, 6.5, 13 and 26 mg of procyanidin.

FIG. 2 relates to a series of graphs that show absolute cumulative food intake of a subject compared to a placebo after 1, 2 and 4 hour administration of hydroxycitric acid (A), procyanidin (B) and procyanidin and hydroxycitric acid (C).

DETAILED DESCRIPTION

One aspect of the invention is a method for the reduction of appetite in mammals, said method comprising administering to said mammal procyanidin, optionally combined with hydroxycitric acid, in an amount effective to reduce the appetite.

Another aspect of the current invention provides a process for the manufacture of a composition, for oral administration, comprising admixing a) a plant extract obtained from one or more plant sources selected from the group consisting of: grape, pine, cocoa, tamarind, tomato, peanut, almond, apple, cranberry and blueberry, wherein said extract comprises between 50 mg and 3 gram procyanidins and wherein said plant extract comprises at least 50 wt. % procyanidin based on the dry weight of the extract and b) between 250 mg and 10 gram of hydroxycitric acid comprising composition, wherein said composition comprises at least 75 wt. % hydroxycitric acid based on dry weight.

Procyanidins

Procyanidines have been known and used especially for their antioxidant properties and their carbohydrase inhibitory effect. It has now surprisingly been found that procyanidins also have appetite reducing properties, when administered to a mammal in a therapeutically effective amount.

Procyanidins are a member of the group of proantbocyanidins. Proanthocyanidins involve procyanidin, prodelphinidin, propelargonidin, proguibourtinidin, profisetinidin, prorobinetinidin, proteracacidin, promelacacidin, proapigeninidin, proluteolinidin and all of the stereoisomers thereof. The procyanidin used in the manufacture of the composition according to the present invention is a polymer, comprising 2 or more units of one or more of the monomers as shown in the following formula.

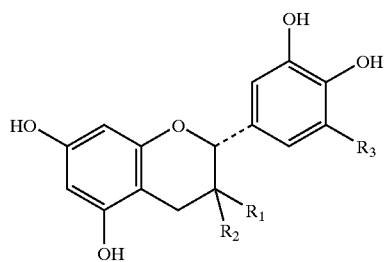

FIG. 1: Structure of procyanidin monomer wherein:
    a. $R_1$=OH, $R_2$=H, $R_3$=H; or
    b. $R_1$=H, $R_2$=OH, $R_3$=H; or
    c. $R_1$=gallic acid ester, $R_2$=H, $R_3$=H; or
    d. $R_1$=H, $R_2$=gallic acid ester, $R_3$=H According to a preferred embodiment the procyanidin is mainly present as a B-type polymer, which have a single interflavanoid bond (in contrast to A-type procyanidin polymers, which have a second interflavaoid bond). Even more preferably at least 70 mol % of the procyanidin polymers are present as B-type polymers.

Procyanidin: Source

Procyanidins can be easily obtained from various sources. Preferably the procyanidins are obtained from a natural, more preferably a plant source. Preferably the procyanidins are obtained from a plant source selected from the group consisting of grape, pine, cocoa, tamarind, tomato, peanut, almond, apple, cranberry, blueberry or mixtures thereof, especially from the group consisting of pine bark, grape seed, tamarind seed husk, cocoa bean, apple peel, apple pericarp or mixtures thereof and most preferred from grape seed and/or pine bark.

Procyanidins: Extract

Many plant sources of procyanidins comprise very low levels of procyanidins. In order to accomplish the desired appetite reducing effect, vast amounts of raw plant material would have to be consumed. The use of an extract of one of the procyanidin sources may avoid such discomfort. An additional advantage of the use of a more concentrated form of procyanidins, e.g. in the form of an extract, resides in the fact that procyanidins may be administered without co-administering a significant amount of caloric plant material. More importantly, however, the inventors believe that the use of compositions having a increased weight percentage of procyanidins provides an increased appetite reducing effect compared to procyanidin containing compositions having a lower weight percentage procyanidins. Preferably the procyanidin containing plant extract used in the current invention comprises at least 25 wt. %, more preferably at least 50 wt. %, even more preferably at least 60 wt. %, especially at least 80 wt. % procyanidin based on the dry weight of the extract.

Procyanidin: Dosage

In accordance with a preferred embodiment, a dosage comprising between 0.5 and 100 mg procyanidin per kg body weight should be administered to a mammal. Typically said mammal would have a body weight above about 12 kg. More preferably the dosage is between 2 and 30 mg procyanidin per kg body weight, even more preferably between 3 and 20 mg procyanidin per kg body weight, especially between 5 mg and 10 mg procyanidin per kg body weight.

For human subjects above an age of about 10 years, an appetite reducing dosage of procyanidin is between 80 mg and 10 g procyanidin, preferably between 100 mg and 5 gram, more preferably between 150 mg and 3 gram, most preferably between about 200 mg and 2 gram per dose, especially between 250 mg and 1 gram per dose.

For human subjects of between about 4 and 15 years, an appetite reducing dosage of procyanidin, preferably apple procyanidin, is between 40 mg and 4 g procyanidin, preferably between 50 mg and 2 gram, more preferably between 60 mg and 1 gram, most preferably between about 75 mg and 500 mg per dose, especially between 90 mg and 300 mg.

According to a preferred embodiment, the appetite reducing composition comprising procyanidin, optionally combined with hydroxycitric acid, comprises at least 1 wt. % procyanidin based on dry weight, more preferably at least 2 wt. %, even more preferably at least 5 wt. %, most preferably at least 8 wt. %, especially at least 12.5 wt. %.

Although the exact effective appetite reducing dosage for use in mammals other than humans would have to be determined in these mammals, such as cats, dogs etc, with the current disclosure this is well within the capabilities of the skilled person.

Procyanidin and HCA: Synergism

It was found that the dose of procyanidin required for inducing an appetite reducing effect can be decreased through the co-administration of hydroxycitric acid. This is especially desirable, since it was found that the ingestion of vast amounts of procyanidin may lead to undesirable side effects such as intestinal stress. It was surprisingly found that the appetite reducing effect of procyanidin is increased by hydroxycitric acid (HCA) and that, similarly, the appetite reducing effect of hydroxycitric acid (HCA) is increased by procyanidin. This provides the possibility to decrease the appetite reducing dosage of both procyanidin and hydroxycitric acid.

This synergistic effect was shown by co-administering a non-appetite reducing dosage of procyanidins and a non-appetite reducing dosage of hydroxycitric acid. Both the non-appetite reducing amount dosage of procyanidins and the non-appetite reducing dosage of HCA did not show any significant appetite reducing effect. Surprisingly, when coadministered, these dosages had a significant appetite reducing effect, showing the synergistic effect of HCA and procyanidin.

Procyanidin+HCA: Dosage of procyanidin

Although HCA and procyanidin show synergistic effects, procyanidin and HCA are to be administered in significant amounts in order to provide an appetite reducing effect. It is the inventors belief that for a mammal having a body weight above 25 kg, between 0.5 mg and 30 mg procyanidin per kg body weight of the mammal should be coadministered with HCA to provide an appetite reducing effect. Preferably, between 0.75 mg and 20 mg procyanidin per kg body weight of the mammal, more preferably between 1 mg and 12 mg procyanidin per kg body weight of the mammal, even more preferably between 2 mg and 8 mg procyanidin per kg body weight of the mammal.

For a human, an appetite reducing dosage of procyanidin, when coadministered with hydroxycitric acid, is preferably between 40 mg and 4 g, more preferably between 50 mg and 3 gram, even more preferably between 75 mg and 2 gram, most preferably between about 100 mg and 1 gram per dose, especially between 150 mg and 750 mg.

Procyanidin+HCCA: Dosage HCA

Where in this application the term hydroxycitric acid (HCA) is mentioned, hydroxycitric acid, its precursors (e.g. salts), metabolites or mixtures thereof are meant. Preferably calcium or potassium hydroxycitrate or mixtures thereof are used.

HCA is preferably used in a dose of between 2 mg and 250 mg per kg body weight, more preferably in a dose between 4 mg and 150 mg per kg body weight, even more preferably in a dose between 10 mg and 90 mg per kg body weight. For a human subject the quantity of HCA per dose would thus typically be between 100 mg and 20 g, preferably between 250 mg and 10 gram, more preferably between 400 mg and 6 gram, even more preferably between 500 mg and 4 gram per dose.

According to a preferred embodiment, the HCA containing raw material (source material) used to provide the HCA contains a high level of HCA. The use of such a relatively pure form of HCA offers the possibility to provide a fairly concentrated form of HCA after admixture with procyanidin. It is the inventors belief that an increased weight percentage of HCA in the appetite reducing composition increases the appetite reducing effect compared to a composition having a lower weight percentage HCA. Additionally, the usage of a relatively pure hydroxycitric acid source reduces the amount of hydroxycitric acid comprising raw material that is required for achieving the appetite reducing effect. Thus the dosage weight of the appetite reducing composition may be kept relatively low, enabling the preparation of a (single dose) appetite reducing composition in the form of a tablet, pill or capsule. Additionally it was found by the current inventors that substantially pure HCA has an unexpected increased appetite reducing effects compared to HCA compositions comprising a lower weight percentage HCA. Relatively pure HCA is believed to provide improved synergistic effects when coadministered with Procyanidin. Preferably, the relatively pure HCA comprises at least 50-wt. %, more preferably at least 60-wt. %, even more preferably at least 75-wt. %, especially at least 95-wt-% HCA based on the dry weight of the HCA containing raw material used.

Preferably, a highly soluble and/or synthetic HCA is used. It is the inventors belief that an increased solubility of the HCA contributes to the appetite reducing effect of hydroxycitric acid, through the increased bioavailability.

Hydroxycitric acid exists in two forms, the free acid form and the lactone form. The free acid form is biologically active and the lactone form is inactive. The HCA containing raw material used to provide the HCA preferably comprises below 5 wt. % HCA in lactone form, preferably below 3 wt. %, even more preferably below 2 wt. %.

Administering

Generally, an individual's feelings and sensations between the start of a first meal and the next meal go through different phases. A set of sensations and sensations is usually discriminated within the art. If satiety is evaluated, several phases can be used to express the satiety after a meal. These can be termed very full, full, appetite and hungry. Preferably the procyanidin, optionally combined with HCA, is administered in the phases appetite, hunger or at the end of the full phase, more preferably in the appetite or hunger phase.

In contrast to the actions of procyanidin as described in the art, such as the carbohydrase and lipase inhibitory effect, it was surprisingly found that procyanidin is capable of reducing the appetite, when administered in an appetite reducing amount. Normally, functional ingredients having e.g. carbohydrase and lipase inhibitory effects have to be administered shortly before or during a meal in order to provide an effect. Preferably, the procyanidin, optionally comprising hydroxycitric acid, is administered after the meal, when a feeling of hunger appears or when the feeling of hunger is likely to appear within a short period. Preferably, the procyanidin, optionally comprising HCA, is administered about 1–8 hours, more preferably about 2–6 hours after consumption of a meal. Typically the procynadin is administered between 1 hour after one meal and 1 hour prior to the next meal.

The present invention provides procyanidin, optionally in combination with HCA, which can be ingested at any time during the day or night, however, in most cases after consumption of a meal and at least 1 hour before the next meal, assuming most humans consume a meal at around 8 AM, 1 PM and 5 PM, the procyanidin, optionally combined with HCA is best consumed between 9 and 12 AM, between 2 and 4 PM and/or between 7 and 12 PM, when the use is aimed at preventing, reducing or postponing the hungry feeling.

Alternatively, the procyanidin can be taken shortly before the meal or even during a meal, when the meal is expected to provide insufficient satisfaction, e.g. when the subject is subjected to a weight loss program.

Whenever the term dose or dosage is used within this disclosure, any dosage form is encompassed which can be administered orally, within a fairly narrow time span. Whenever reference is made to a certain quantity that is administered per dose or dosage, said quantity is preferably administered within one hour, more preferably within 15 minutes, even more preferably within 5 minutes.

The medicament comprising an appetite-reducing amount of procyanidin, optionally also comprising HCA, may be administered orally in the form of a pill, tablet, capsule, liquid composition, or admixed in a meal, more preferably in the form of a pill, tablet, capsule or the like.

A dose or dosage, when in the form of a pill, capsule or tablet or the like, can consist of more than one pill, capsule, table or the like. According to a preferred embodiment, a dose or dosage does not consist of more than 3 tablets, capsules, pill or the like, even more preferably the dose consists of a single pill, capsule, tablet or the like.

Use

The present invention is especially aimed at the reduction or prevention of appetite and/or feelings of hunger. The method according to the invention can, for example, be used by subjects having the desire to reduce appetite, induce satiety, satisfy hunger or reduce craving urges. The appetite reducing amount of procyanidins can be used either alone or in combination with other substances contributing to weight loss or general health, such as for example herbal preparations, vitamins, minerals, fibers and antioxidants.

Since appetite reduction is an important means through which overweight can be prevented or treated, the appetite-reducing medicament can be used either in a preparation essentially directed towards the reduction of the appetite or in a preparation or program for reducing the weight in a mammal wherein also other active or functional substances are (co)administered to the subject.

The administration of an appetite reducing amount of procyanidin will reduce the appetite of said mammal and consequently will reduce the caloric intake.

The composition of the present invention can be administered to subjects participating in a weight loss program for reduction of the adverse side effects which can be experienced during such a program. Strong appetite or feelings of hunger are often experienced by subjects participating in a weight loss program. Such discomfort can be relieved by administering an appetite reducing amount of Procyanidin, optionally combined with HCA during the time the subject is subjected to the weight loss program.

Additionally appetite reducing agents are useful in several other applications. These can be used to provide comfort to subjects having limited access to foodstuffs, such as for example military personal during a long mission.

EXAMPLES

Example 1

Appetite Reducing Effects of Procyanidin

The appetite suppressive effects of a procyanidin containing extract from pine bark, comprising 65 wt. % procyanidin was tested in male Wistar rats. In a placebo-controlled cross-over study, either placebo or increasing dosages of procyanidins were administered as a single bolus intragastrically at 30 min before onset of the active (dark) period. Subsequently, voluntary food intake was recorded continuously for 48 hours. Following this period, the experiment was repeated as part of the cross-over design (that is, rats which first received the procyanidins now received the placebo and vice versa).

Results are shown as relative food intake when compared with the placebo treatment. FIG. 1 show a clear dose-dependent decrease in food intake shortly after administration of the procyanidin extract.

A dose of about 26 mg procyanidin per kg rat resulted in a significant ($p<0.05$) reduction of food intake for over 12 hours, indicating a reduced appetite.

Example 2

Appetite Reducing Effects of Coadministered Procyanidin and Hydroxycitric Acid

The appetite suppressive effects of a combination of procyanidin (pine bark extract containing 65 wt. % procyanidin) and hydroxycitric acid (Regulator™ ex HOB Ireland, Dublin, Ireland) was tested in male Wistar rats. In a placebo-controlled cross-over study, either 13 mg procyanidin per kg rat (A), 155 mg hydroxycitric acid per kg rat (B) or 13 mg procyanidin per kg rat and 155 mg hydroxycitric acid per kg rat (C) were administered as a single bolus intragastrically at 30 min before onset of the active (dark) period.

Subsequently, voluntary food intake was recorded continuously for 48 hours. Following this period, the experiment was repeated as part of the cross-over design (that is, rats which first received the procyanidins now received the placebo and vice versa).

Results are shown as absolute cumulative food intake after 1,2 and 4 hours (see FIG. 2). Statistical analysis (paired student t) was made of the data. It can be concluded from the data and the statistical analysis thereof, that the administration of hydroxycitric acid (A) or procyanidin (B) did not result in a significant decrease in absolute cumulative food intake. The coadministration of hydroxycitric acid and or procyanidin resulted in a significantly ($p<0.05$) decreased absolute cumulative food intake. These results show the synergistic appetite reducing effects of procyanidin and hydroxycitric acid.

Example 3

Appetite Reducing Supplement for Humans

Soft gelatin capsule containing, 800 mg Vitis vinifera extract (comprising 85 wt. % procyanidins)

Example 4

Appetite Reducing Supplement for Humans

Soft gelatin capsule containing, 400 mg pycnogenol (comprising 65 wt. % procyanidins)

800 mg synthetic hydroxycitric acid, comprising below 2 wt. % hydroxycitric acid in the lactone form Example 5

Anti-Craving Supplement for Humans

Tablet containing 800 mg Vitis vinifera extract (comprising 85 wt. % procyanidins)

250 mg Gymema sylvestre extract (comprising 25 wt. % gymnemic acid)

Example 6

Appetite Reducing Supplement for Humans

Tablet containing 200 mg Vitis vinifera extract (comprising 85 wt. % procyanidins)

700 mg synthetic hydroxycitric acid, comprising below 2 wt. % hydroxycitric acid in the lactone form

Example 7

Appetite Reducing Bar for Children

Cereal bar containing:

50 mg procyanidins in the form of apple chunks 30 gram oat bran

What is claimed is:

1. A process for the manufacture of a composition, for oral administration, comprising admixing:
   a) a plant extract obtained from one or more, plant sources selected from the group consisting of grape, pine, cocoa, tamarind, tomato, peanut, almond, apple, cranberry and blueberry, wherein said plant extract comprises at least 50 weight percent procyanidin based on the dry weight of the extract and
   b) an hydroxycitric acid containing raw material wherein said hydroxycitric acid containing raw material comprises at least 50 weight percent hydroxycitric acid based on dry weight of the hydroxycitric acid containing raw material
      forming an admixture comprising a) and b) to produce a composition for oral administration which when administered to a mammal can provide per dosage between 0.5 to 100 mg procyanidin per kg of body weight and between 2 to 250 mg hydroxycitric acid per kg of body weight.

2. A method for reducing appetite in a mammal, said method comprising administering to said mammal an appetite reducing effective amount of the composition produced by the method of claim 1.

3. The method according to claim 2, wherein between 0.5 and 100 mg procyanidin per kg of body weight is administered to the mammal per dosage.

4. The method according to claim 2, wherein between 2 to 250 mg hydroxycitric acid per kg of body weight in combination with between 0.5 to 30 mg procyanidin per kg of body weight is administered to the mammal per dosage.

5. The method according to claim 2, wherein the method comprises administering to the mammal per dosage a combination of between 0.5 and 30 mg procyanidin per kg of body weight and between 4 and 150 mg hydroxycitric acid per kg of bodyweight.

6. The method according to claim 1, wherein the procyanidin is obtained from one or more plant sources selected from the group consisting of grape seed, pine bark, tamarind husk, cocoa bean, apple pericarp and apple peel.

7. The method according to claim 2, wherein the procyanidin, combined with hydroxycitric acid, is administered in the form of a composition that comprises at least 1 weight percent procyanidin, based on dry weight of the composition.

8. The method according to claim 2, wherein the composition is administered between 1 hour after one meal and 1 hour prior to the next meal.

9. The method according to claim 2, wherein the composition is administered in the form of a tablet, pill or capsule.

10. The method according to claim 2, wherein the hydroxycitric acid in the composition is provided by a hydroxycitric acid containing raw material containing at least 60 weight percent hydroxycitric acid based on dry weight.

* * * * *